United States Patent [19]

Ogawa et al.

[11] 4,432,373
[45] Feb. 21, 1984

[54] ELECTRONIC BLOOD PRESSURE MEASURING APPARATUS

[75] Inventors: Hiroshi Ogawa, Nagaokakyo; Syozi Kimura, Kameoka; Yoshinori Miyawaki, Yawata, all of Japan

[73] Assignee: Omron Tateisi Electronics Company, Hanazono, Japan

[21] Appl. No.: 338,255

[22] Filed: Jan. 11, 1982

Related U.S. Application Data

[63] Continuation of Ser. No. 122,740, Feb. 19, 1980, abandoned.

[51] Int. Cl.³ .............................................. A61B 5/02
[52] U.S. Cl. .................................................. 128/680
[58] Field of Search ............................... 128/680–686; 324/57 N; 340/657

[56] References Cited

U.S. PATENT DOCUMENTS

| 2,827,040 | 3/1958 | Gilford | 128/682 |
| 3,905,354 | 9/1975 | Lichowsky | 128/681 |
| 3,906,939 | 9/1975 | Aronson | 128/680 |
| 4,005,701 | 2/1977 | Aisenberg et al. | 128/680 |
| 4,112,929 | 9/1978 | Affeldt et al. | 128/680 |
| 4,214,589 | 7/1980 | Sakamoto et al. | 128/680 |
| 4,216,779 | 8/1980 | Squires et al. | 128/682 |

Primary Examiner—Kyle L. Howell
Assistant Examiner—Francis J. Jaworski
Attorney, Agent, or Firm—Wegner & Bretschneider

[57] ABSTRACT

Electronic blood pressure measuring apparatus comprising pressure detecting means operatively connected with a cuff for detecting a pressure of the cuff, Korotkoff sound detecting means asociated with the cuff for detecting any Korotkoff sound contained in a sphygmus sound and generating a Korotkoff sound signal, verifying means operative in response to the Korotkoff sound output detector signal generated from the Korotkoff sound detecting means for determining systolic and diastolic blood pressures, signal detecting means for detecting the generation of a Korotkoff sound signal by said Korotkoff sound detecting means and generating an output signal, and indicator means operative in response to said output signal from said signal detecting means for displaying the generation of said Korotkoff sound signal.

3 Claims, 2 Drawing Figures

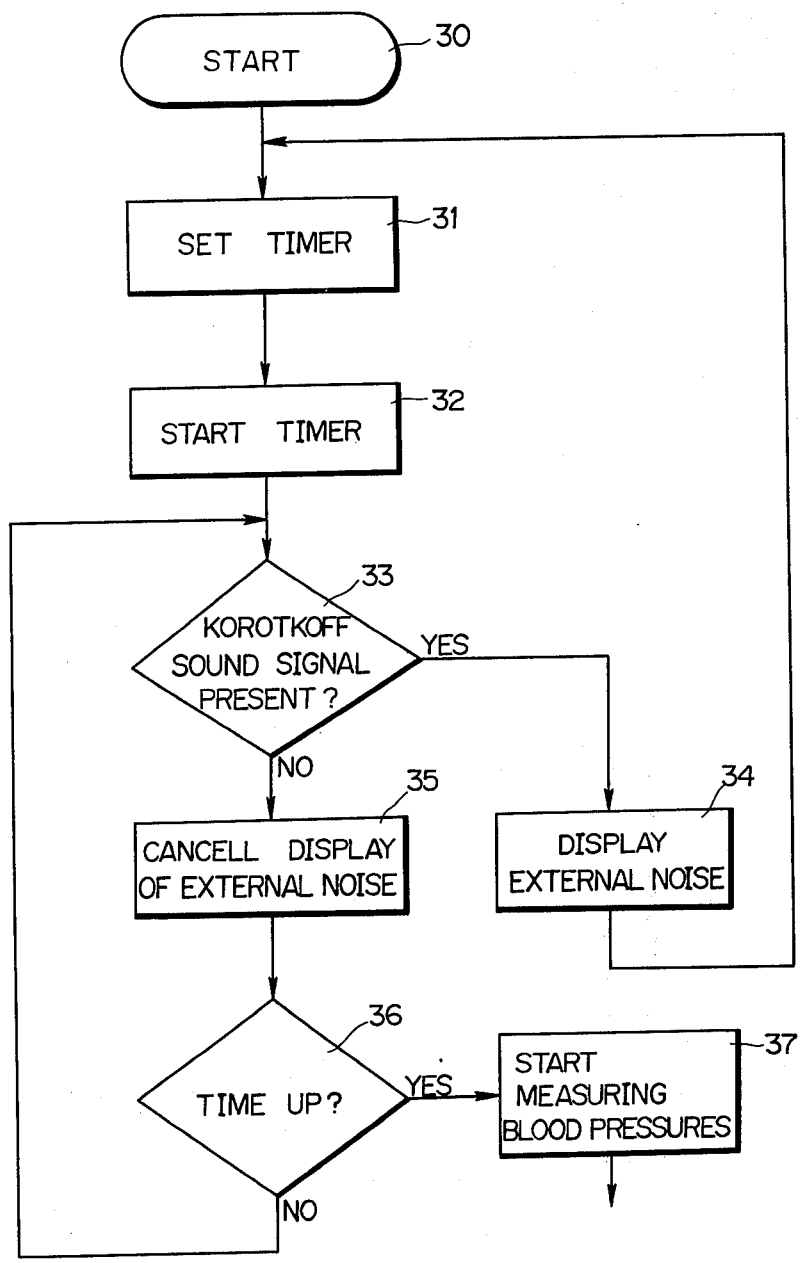

4,432,373

ELECTRONIC BLOOD PRESSURE MEASURING APPARATUS

This application is a continuation of application Ser. No. 122,740 filed Feb. 19, 1980, now abandoned.

BRIEF SUMMARY OF THE INVENTION

The present invention relates to an electronic blood pressure measuring apparatus, and more particularly to an improved apparatus capable of measuring the systolic and diastolic blood pressures of a patient without being influenced by noise and precisely displaying the measured pressures.

In a conventional electronic blood pressure measuring apparatus comprising an inflatable cuff and a microphone associated with the cuff, the cuff is wrapped about the upper arm of a patient or person, and the microphone detects Korotkoff sounds to generate Korotkoff sound signals. The cuff pressure is increased above a pressure believed to be the systolic blood pressure, and then allowed to decrease. The pressure at which the Korotkoff sounds first appear in the course of pressure decrease is taken as the systolic blood pressure. The Korotkoff sounds continue to appear with the decrease of the cuff pressure. The pressure at which the Korotkoff sounds disappear is taken as the diastolic blood pressure. The Korotkoff sounds are very delicate and readily influenced by external noise, which has been a cause of error in blood pressure determinations. Moreover, the Korotkoff sounds are complicated, and it is generally acknowledged to be virtually impossible to separate the Korotkoff sounds from the external noise. The external noise influencing blood pressure determinations not only arises from movements of the patient but also includes ambient sound noise, radio noise and so forth. The conventional blood pressure measuring apparatus is used not only by the doctor or nurse, but also by individuals at home where the measuring is influenced very much by room noise generated from television sets, radio receivers or their family. Accordingly, to obtain accurate measurements, it is important to find a suitable environment for measuring blood pressures.

It is, therefore, a primary object of the present invention to provide an electronic blood pressure measuring apparatus capable of measuring systolic and diastolic pressures accurately without being influenced by external noise due to the environment.

It is a further object of the present invention to provide an electronic blood pressure measuring apparatus which detects external noise and provides the observer with an indication of the existence of such external noise.

It is another object of the present invention to provide an electronic blood pressure measuring apparatus utilizing a microprocessor wherein the apparatus begins to measure blood pressures unless a Korotkoff sound signal is generated therein for a predetermined period of time.

Other objects and advantages of the present invention will be apparent upon reference to the following description in conjunction with the accompanying drawings, in which:

BRIEF DESCRIPTION OF DRAWINGS

FIG. 2 is a flow chart illustrating the operation of an electronic blood pressure measuring apparatus as another embodiment of the present invention.

DETAILED DESCRIPTION

Figure 1:
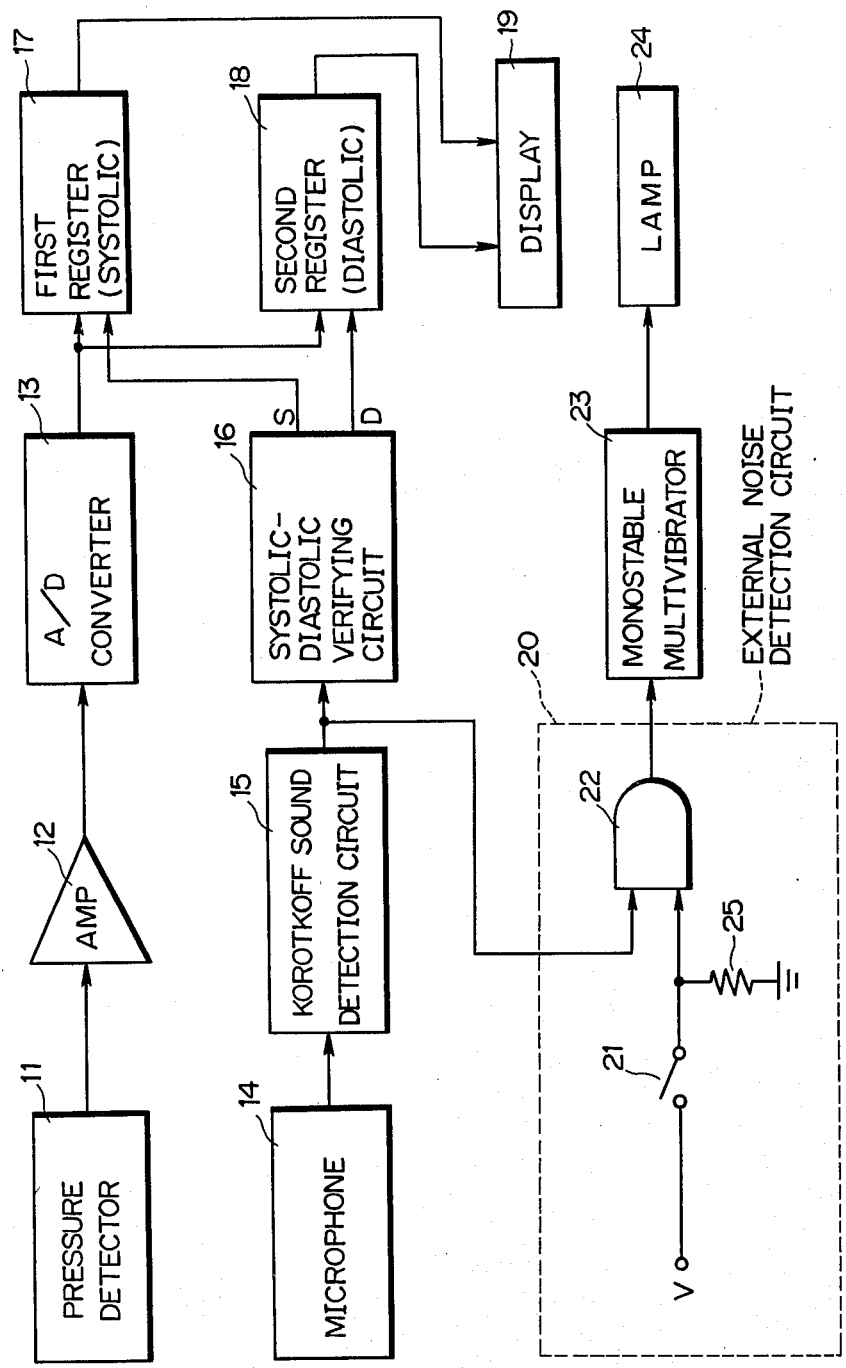
FIG. 1 is a block diagram of an electronic blood pressure measuring apparatus as a preferred embodiment of the present invention.

Referring, now, to FIG. 1, a pressure detector 11 is operatively connected with an inflatable cuff (not shown) to generate an analog output signal in response to the actual pressure in the inflatable cuff. A semi-conductor sensor is preferably employed as the pressure detector 11. The cuff is wrapped around the upper arm of the body, and is connected through a rubber tube with a simple rubber bulb or a powered pump so as to occlude the upper arm containing an artery. The pressure detector 11 is connected through an amplifying circuit 12 to an A/D converter 13 wherein the analog output signal from the detector 11 is converted into a digital signal. The converted digital signal is applied to first and second registers 17 and 18 which are adapted to store the digital signal temporarily. The stored signal is applied to a display device 19 which is adapted to numerically display systolic and diastolic blood pressures. The first and second registers 17 and 18 are for storing systolic and diastolic blood pressure signals, respectively.

A microphone 14 is wrapped in the inflatable cuff so as to detect sphygmus sounds containing Korotkoff sounds and generate output signals. The output signals from the microphone 14 are applied to a Korotkoff sound detection circuit 15 which extracts Korotkoff sound signals from the output signals. The circuit 15 includes an amplifying circuit, a band-pass filter and a pulse shape circuit. Each time a Korotkoff sound is generated from the occluded arm of the body, the circuit 15 generates a Korotkoff sound signal in a pulse waveform and supplies a systolic-diastolic blood pressure verifying circuit 16 with the Korotkoff sound signal. The verifying circuit 16 generates a systolic blood pressure signal S, which is applied to the first register 17, when a first Korotkoff sound signal is generated from the circuit 15 during the decrease of cuff pressure which has been increased above the systolic blood pressure. After generating the systolic signal S, the verifying circuit 16 generates a timing signal D, which is applied to the second register 18, each time a subsequent Korotkoff sound signal is generated from the circuit 15. When the systolic pressure signal S is applied to the first register 17 as a timing signal, the register 17 stores a current output signal from the circuit 13. The output signal stored then in the register 17 is applied to the display 19 to be displayed as the systolic blood pressure in numerals. Each time the timing signal D is applied to the second register 18, the register 18 stores an output signal being then generated from the circuit 13 and applies the stored signal to the display 19. The signal stored in the register 18 is updated by each timing signal D generated from the circuit 16, whereby an updated blood pressure is displayed at the display 19. When the Korotkoff sounds cease to be generated as the cuff pressure drops further, the circuit 16 ceases to generate the timing signal D and the signal stored in the second register 18 is not updated. The last signal stored in the register 18 represents the pressure of the cuff at the exact time point when the Korotkoff sounds ceased to appear, and is applied to the display 19 where it is displayed as the diastolic blood pressure.

A signal detection circuit 20 including a check switch 21 and an AND circuit 22, which detects if the circuit 15 generates Korotkoff sound signals. The AND circuit 22 is connected at input terminals thereof to switch 21 and circuit 15, and at output terminal thereof to a monostable multivibrator 23. The output signal generated from the multivibrator 23 is applied to an signal noise indicator lamp 24 to be lighted. Normally, the switch 21 is open and the input terminal of circuit 22 connected to the switch 21 is grounded through a resistor 25.

The check switch 21 is supplied with a predetermined reference voltage V. When the switch 21 is turned on, the voltage V is applied to the AND circuit 22, so that sound signals generated from the circuit 15 are applied through the circuit 22 to the vibrator 23 as trigger pulse signals. In response to each of the trigger pulse signals, the multivibrator 23 passes into a semistable state from a stable state, and generates an output signal so as to light the indicator lamp 24 for a time period which is determined by the circuit constants of the multivibrator 23, i.e. until the multivibrator 23 returns to the stable state from the semistable state. Thus, when the switch 21 is turned on, the lamp 24 flickers in response to lack of a Korotkoff sound signal from the circuit 15.

An inquiry of whether or not the Korotkoff sound detection circuit 15 generates Korotkoff sound signals may be made at any desired time point by turning on the switch 21. Turning on the switch 21, when any Korotkoff sounds ought not to be detected, e.g. before wrapping the cuff around the arm of a person or before inflating the cuff after wrapping, enables one to known if the detection circuit 15 erroneously detects external noise and erroneously generates a Korotkoff sound signal. If the lamp 24 is lighted when any Korotkoff sound signal cannot be generated, the flickering of indicator lamp 24 allows the observer to notice that the circuit 15 erroneously generates Korotkoff sound signals in response to external noise. After correcting the surroundings of the blood pressure measuring apparatus, for example, by removing the source of noise that is believed to influence the circuit 15, that is, after switching off the television or radio set, stopping the conversation or removing any other source of noise, the observer may recheck to see, by turning on the switch 21 again and finding that the indicator lamp 24 is not lighted, that the circuit 15 does not erroneously pick up noise. Accordingly, if the apparatus measures blood pressures under the corrected surroundings, an accurate measurement can be expected without being influenced by noise.

If the switch 21 is turned on at any time point other than during a blood pressure measurement, the observer may check if the measuring apparatus erroneously detects noise due to the surroundings. The switch 21, however, may be cooperatively associated with a power switch of the apparatus. In this arrangement, the switch 21 is turned on as the power switch is turned on, and is automatically turned off after a predetermined time has elapsed. Such a construction can be easily designed by using a relay circuit and a timer circuit.

In FIG. 2, there is shown a partial flow chart for illustrating the operation of an external noise detection circuit portion of an electronic blood pressure measuring apparatus utilizing a microprocessor, which is another embodiment of the present invention. This measuring apparatus is designed to advance to the determination of systolic and diastolic blood pressures only after confirming the absence of the possibility of erroneous measurements due to noise. The measuring apparatus includes like components shown in FIG. 1, and further includes a timer and a memory. The timer and memory, may each be an independent control component, or may be a predetermined area of the microprocessor. The memory stores a control program as shown in FIG. 2.

In a step 30, a power switch of the measuring apparatus is turned on and a sequence advances to a step 31. In step 31, the timer sets a predetermined time period. In a step 32, the timer is started and a sequence advances to a step 33 wherein it is inquired if a Korotkoff sound detection circuit generates a Korotkoff sound signal. If there is a Korotkoff sound signal, a YES response is applied to a step 34 wherein an existence of a signal is indicated by a display device. The display device may be a flickering lamp or a display device for displaying blood pressures. The sequence from step 34 is then returned to the step 31 and the timer is again set. A NO response from step 33 is applied to a step 35 wherein the indication of the existance of noise, if any, is cancelled. In a step 36, it is inquired if the predetermined time period set by the timer has expired. A NO response from step 36 is applied to step 33, and the sequence from steps 33 through 36 is repeated in a predetermined cycle. A YES response from step 36 is applied to a step 37 wherein the measuring apparatus starts measuring systolic and diastolic blood pressures.

Thus if no Korotkoff sound signal has been generated during the predetermined time period set by the timer, the sequence advances to the step 37. This advance to step 37 takes place even when a Korotkoff sound signal has been generated and a noise indication has been displayed, only if the user has removed the noise by changing the place of determination and, thereafter, there has been no Korotkoff signal generation for the abovementioned predetermined time.

In the above embodiments, a lamp or display device indicates that the Korotkoff sound signal detection circuit is erroneously detecting noise as a Korotkoff sound signal. However, any other suitable device, for instance, a buzzer may be employed for the purpose. The systolic-diastolic blood pressure verifying circuit (16) may be any other suitable circuit or device, such as a device adapted to ensure that only when more than one Korotkoff sound signals appear in two seconds, the pressure corresponding to the first of said Korotkoff signals is taken as the measured systolic pressure and only when a series of Korotkoff sound signals are no longer followed by another Korotkoff sound signal in two seconds, the pressure corresponding to the last of said Korotkoff sound signals is taken as the diastolic pressure.

The above description is merely illustrative of the present invention; the present invention is not limited to the above-described embodiments, and various changes and modifications may be made in the invention without departing the spirit and scope thereof.

What is claimed is:

1. In an electronic pressure measuring apparatus comprising pressure detecting means operatively connected with a cuff for detecting a pressure at the cuff, Korotkoff sound detecting means associated with the cuff for detecting any Korotkoff sound output signal and verifying means operative in response to the Korotkoff sound detecting means output signal generated by the Korotkoff sound detecting means for determining systolic and diastolic blood pressures, the improvement comprising signal detecting means for detecting the generation of a Korotkoff sound detecting means output signal by said Korotkoff sound detecting means and generating a signal detecting means output signal and indicator means operative in response to said signal detecting means output signal for displaying the generation of said Korotkoff sound detecting means output signal, wherein said signal detecting means includes a check switch and an AND circuit adapted to receive both an output signal from said check switch and said Korotkoff sound detecting means output signal, the check switch further being adapted so that prior to a blood pressure measurement the check switch is closed and remains in an "on" position for a predetermined time period, and wherein said signal detecting means further includes a display means operative in response to the AND circuit that signals the generation of said Korotkoff sound detecting means output signal by said indicator means as a warning signal of an improper measurement condition.

2. Electronic blood pressure measuring apparatus according to claim 1 which further comprises a power switch and wherein said check switch is adapted to be turned on in association with said power switch and remain on for a predetermined time period.

3. Electronic blood pressure measuring apparatus according to claim 1, further comprising a microprocessor as part of the signal detecting means, said microprocessor including a timer for determining passage of said predetermined time period, and wherein said Korotkoff sound detecting means output signal is generated in response to Korotkoff sounds and external noise, said microprocessor enabling the apparatus to start the blood pressure measurement if no Korotkoff sound detecting means output signal is generated during said predetermined time period.

* * * * *